(12) United States Patent
Fontaine

(10) Patent No.: US 9,622,908 B2
(45) Date of Patent: Apr. 18, 2017

(54) DEVICE AND METHOD FOR COOLING A PATIENT

(75) Inventor: Guy Fontaine, Saint Mandé (FR)

(73) Assignee: Schiller Medical S.A.S., Wissembourg (FR)

( * ) Notice: Subject to any disclaimer, the term of this patent is extended or adjusted under 35 U.S.C. 154(b) by 277 days.

(21) Appl. No.: 14/360,823

(22) PCT Filed: Aug. 14, 2012

(86) PCT No.: PCT/EP2012/065843
§ 371 (c)(1),
(2), (4) Date: May 27, 2014

(87) PCT Pub. No.: WO2013/079227
PCT Pub. Date: Jun. 6, 2013

(65) Prior Publication Data
US 2014/0330197 A1 Nov. 6, 2014

(30) Foreign Application Priority Data

Dec. 2, 2011 (EP) .................................... 11191745

(51) Int. Cl.
*A61M 37/00* (2006.01)
*A61F 7/10* (2006.01)
(Continued)

(52) U.S. Cl.
CPC ................. *A61F 7/10* (2013.01); *A61F 7/12* (2013.01); *A61M 5/14* (2013.01); *A61M 5/44* (2013.01); *A61M 11/04* (2013.01); *A61M 16/0461* (2013.01); *A61M 16/0484* (2014.02); *A61M 19/00* (2013.01); *A61F 2007/0006* (2013.01); *A61F 2007/0064* (2013.01);
(Continued)

(58) Field of Classification Search
CPC ................. A61F 7/12; A61F 2007/0064; A61F 2007/0006; A61M 19/00; A61M 2202/03; A61M 2205/3606; A61M 2210/0693; A61M 5/44; A61M 25/003; A61M 25/007; A61M 2025/0073
See application file for complete search history.

(56) References Cited

U.S. PATENT DOCUMENTS 5,755,756 A * 5/1998 Freedman, Jr. ........... A61F 7/10
607/105
2001/0020159 A1* 9/2001 Barbut ................ A61M 27/006
604/500
(Continued)

FOREIGN PATENT DOCUMENTS

WO 2008/063179 5/2008
WO 2011/115964 9/2011

*Primary Examiner* — Emily Schmidt
(74) *Attorney, Agent, or Firm* — Davis & Bujold PLLC; Michael J. Bujold

(57) ABSTRACT

A device is provided for cooling intra nasally the brain of a patient, in particular of a patient suffering from cardiovascular emergency. The device comprises a pressurized gas container for containing a gas or a mixture of gases, and at least one cannula with a lumen, a proximal opening and at least one distal opening. The cannula is for introduction into the patient's nasopharynx. Upon operation, gas expands adiabatically upon exiting from the at least one cannula, thereby cools and provides a coolant effect on the nasopharynx and inside the nasal cavity.

43 Claims, 15 Drawing Sheets

(51) Int. Cl.
*A61M 5/44* (2006.01)
*A61M 11/04* (2006.01)
*A61M 16/04* (2006.01)
*A61F 7/12* (2006.01)
*A61M 19/00* (2006.01)
*A61M 5/14* (2006.01)
*A61F 7/00* (2006.01)
*A61M 5/00* (2006.01)

(52) U.S. Cl.
CPC . *A61F 2007/0096* (2013.01); *A61F 2007/126* (2013.01); *A61M 16/0497* (2013.01); *A61M 2005/006* (2013.01); *A61M 2202/0225* (2013.01); *A61M 2202/0283* (2013.01); *A61M 2202/03* (2013.01); *A61M 2210/0618* (2013.01); *A61M 2210/0625* (2013.01)

(56) References Cited

U.S. PATENT DOCUMENTS

| | | | |
|---|---|---|---|
| 2006/0276552 A1* | 12/2006 | Barbut | A61F 7/12 514/743 |
| 2008/0000532 A1 | 1/2008 | Wagner | |
| 2009/0192505 A1* | 7/2009 | Askew | A61B 18/0218 606/21 |
| 2009/0234325 A1* | 9/2009 | Rozenberg | A61F 7/123 604/514 |
| 2009/0259173 A1* | 10/2009 | Wang | A61K 9/0043 604/26 |
| 2010/0324483 A1* | 12/2010 | Rozenberg | A61M 16/045 604/98.01 |
| 2013/0030411 A1* | 1/2013 | Kreck | A61F 7/12 604/514 |

* cited by examiner

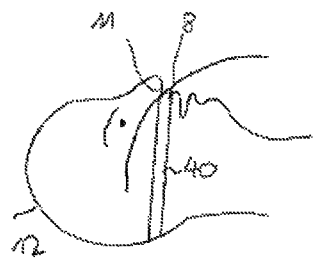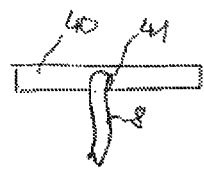
FIG.6a  FIG.6b
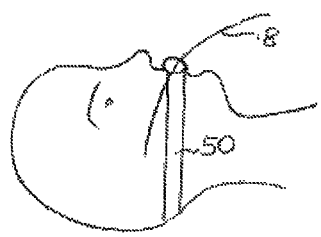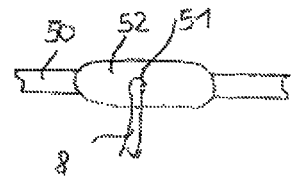
FIG.7a  FIG.7b
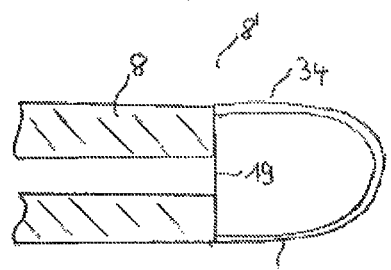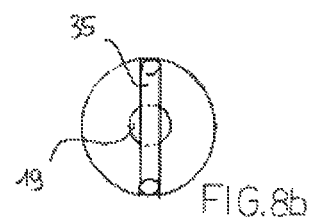
FIG.8a  FIG.8b
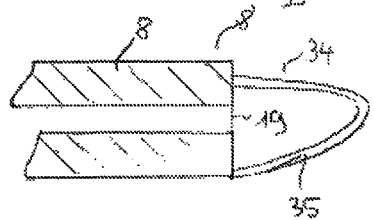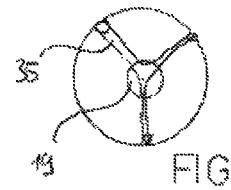
FIG.9a  FIG.9b

DEVICE AND METHOD FOR COOLING A PATIENT

The present invention relates to methods and devices for providing intracorporal and extracorporal cooling to a patient, in particular intranasal and intramouth cooling to protect the brain of a patient, as well as lung cooling to protect the myocardium and other organs of a patient such as kidney, liver and lungs according to the preambles of the independent claims.

It is known, that events that can cause the cerebral perfusion to be impaired can cause permanent brain damage. Events that can cause such an effect can arise due to, for example, cardiac arrest, acute myocardial infarction, ischemic stroke, traumatic injury or neurogenic fever. In the event of cardiac arrest, the most common cause of death during hospitalisation after resuscitation is related to ischemic injury caused by, e. g. anoxic encephalopathy. It is known that the resuscitation of patients suffering from cardiac arrest without neurologic deficit is time critical.

It is also known, that induced therapeutic hypothermia can reduce or prevent damage to the brain in case of impaired cerebral perfusion.

One method of inducing therapeutic hypothermia is the introduction of cooling catheters into the superior and inferior vena cava. This invasive method remains mostly confined to hospital environments, as it requires bulky equipment that cannot be transported in ambulances.

A non-invasive method of inducing therapeutic hypothermia is the use of blankets, vests or wraps that are equipped with a coolant liquid. In another approach, the patient is placed in an ice bath to reduce the body temperature. This method requires the use of heavy and non transportable equipment and provides at the same time for a non-reliable, non-specific cooling effect that is greatly influenced by the patient's body mass.

It is therefore desirable to provide a device and a method for specifically cooling the brain and the body of a patient suffering from an impaired cerebral perfusion immediately after the syncope that can be easily operated by an emergency team in and out of hospital environment.

WO 2008/063179 A1 proposes methods and devices for non-invasive cerebral and systemic cooling. A nebulized liquid is delivered as a mist or spray via the nasal cavities. The cooling effect rests on either direct heat transfer through the nasopharynx, evaporative heat loss and/or haematogenous cooling. The gases produced by evaporation of various forms of per fluorocarbon are used as a cooling media.

WO 2008/094505 A1 describes an apparatus and methods for cooling the brain using a cooled gas. This document discloses a pernasal intubation tube for insertion through the nostrils. The device further features an inflatable occluder. The occluder is adapted to occlude the nasopharynx such as to prevent the passage of liquid from the nasal cavities to the respiratory tract. Venous flow of blood to the brain is increased by applying a pressure device to the exterior of the nose and applying pressure to the angular vein. Cooling of the gas is made with a cooling coil, through which the gas passes or by adiabatic expansion of the gas upon exiting from a pressure container and prior to entering the patient's nasopharynx.

Still, all the methods of the state of the art either rely on potentially hazardous substances or are complicated to use and maintain in a situation of distress, such as that is frequently encountered by emergency personnel and first responders.

It is thus an object of the present invention to overcome the drawbacks of the prior art; in particular to provide a method, a device and a set for cooling the brain or other organs of a patient suffering, or under risk of suffering, from impaired cerebral perfusion that is easy to use, cheap in manufacture and maintenance and can be used with minimal training for first aid situations, particularly on the field and during transportation to the hospital environment.

This object has been solved with a method and a device for intracorporally cooling a patient, in particular for providing intranasal cooling to the brain of a patient according to the independent claims. A patient in the context of the present invention is a mammal suffering or facing a considerable risk of impaired cerebral perfusion. The patient can be a human being in medical, or almost any type of animal in veterinary use. The device is particularly useful for patients suffering from cardiovascular emergency. The device comprises a pressurised gas container for containing a gas or a mixture of gases. The gas container is preferably adapted to withstand the pressure of the gases stored therein. Materials such as carbon steel, stainless steel, aluminium, or composite can be used for that end. In an even more preferred embodiment the gas container is adapted to hold a gas or mixture of gases whereby one gas is in essentially liquid form. The device further comprises at least one cannula sized and shaped for introduction into the patient's nasopharynx, in the patient's mouth or in the patient's trachea. The at least one cannula is from an essentially rod-like shape and can be functionally connected to the pressurised gas container either directly or by means of a flexible, e. g. bendable tube. The at least one cannula can be further sheathed in a soft material, such as silicone or PU for example. In a preferred embodiment, the cannula is of an essentially semi-rigid material, such as PVC or PU or PP for example.

Preferably, the cannula is sized and shaped for introduction into the interior of blood vessels, in particular the vena cava. More preferably, the cannula is adapted as an intravascular expandable balloon and provided with a cooling contact surface.

The pressurised gas container and the at least one cannula are adapted to provide for adiabatic expansion of the gas or mixture of gases upon exit of the gas from the at least one cannula. The at least one cannula features at least one interior lumen and at least two openings, one that functionally connects the cannula to the pressurized gas container and one that functions as exit point of the gas upon operation. In the context of the present invention, the opening of the cannula closer to the pressurized gas container shall be termed the proximal end of the cannula, whereas the end of the cannula featuring the exit for the gas upon operation shall be referred to as the distal end of the cannula. The lumen forms a hollow space inside the cannula and upon operation, i. e. during gas release, is in fluid connection with the inside of the pressurized gas container.

It has been found, that such a device is effective at cooling the brain or other internal areas or organs of a patient, without having to rely on further coolant means.

In a preferred embodiment the gas container and the at least one cannula are connected by a connection means. The connection means are adapted to substantially prevent adiabatic expansion of the gas or mixture of gases upon passage from the container to the at least one cannula. A connection means according to the present invention can comprise individual components, such as a seal or sealant, a valve, a valve guard, a pressure regulator, a flow control, a switch, etc. for operating a valve, as well as stems and springs.

In a preferred embodiment, the connection means further comprises an essentially flexible tube between the pressure bottle and the cannula. The flexible tube preferably has a length of from 50 mm to 1500 mm, more preferably 300 mm. The flexible tube can be of a material that withstands the high pressure of the gases, but still has pliability. Suitable flexible tubes can be manufactured of plastics. Preferably, the flexible tube can have a supporting or strengthening wire mesh incorporated therein.

In a further preferred embodiment the cannula is between 50 and 200 mm long, even more preferably between 60 and 180 mm long, and most preferably the cannula is around 100 mm long. Alternatively, the device can be fitted with a telescopic or exchangeable cannula that can be adapted to the patient's anatomy.

The at least one cannula preferably may comprise at least one distal opening. The distal opening is adapted to enable an adiabatic expansion of the gas when exiting the cannula through the distal opening.

According to a further preferred embodiment the distal end of the cannula may be provided with an extension projecting therefrom. This extension avoids closing of the distal opening if the distal end of the cannula abuts an area of the body of the patient. In particular, this extension may be formed by at least one arch projecting from the distal end of the cannula. There can be one or also a plurality of arches. The arch or the arches may be formed on a cap which is attached to the distal end of the cannula. Alternatively, the extension may be formed by a cap having an outer surface with at least one hole formed therein.

According to another preferred embodiment of the invention, the cannula is made of a plastic material and a metal insert may be arranged at the distal end of the cannula for forming the distal opening. Such a metal insert allows for a more precise definition of the distal opening. Furthermore, it also avoids a retraction of the plastic material leading to a reduced diameter at lower temperatures.

According to still a further embodiment of the invention, for security reasons, the cannula may be chosen such as to have a wall with a wall thickness which can withstand at least a certain minimum pressure, typically which can withstand about the double of the maximum pressure within the gas container. With such an arrangement bursting of the cannula e. g. in case of closed openings can be avoided. However, making the cannula with such a relatively high wall thickness might render the cannula thick and inflexible. As an alternative, preferably, the cannula at its proximal end may be provided with a pressure limiting member. Such pressure limiting member has a reduced diameter such that no adiabatic expansion occurs when the gas passes through this member. Nevertheless, the diameter is chosen such as to limit the maximum inner pressure within the cannula in case of burst of the cannula.

In a preferred embodiment the at least one cannula comprises at least one further opening beside the distal and proximal openings. The opening is adapted to enable adiabatic expansion of the gas or mixture of gases exiting the cannula. In a preferred embodiment the at least one further openings are placed in relative proximity to the distal opening and arranged evenly close to said end of the cannula. In a further preferred embodiment the cannula has more than two openings. Preferably the cannula has from two to thirty additional openings. In an even more preferred embodiment, the cannula has from two to ten additional openings. The openings are constructed such as to provide for adiabatic expansion of the gas upon exiting the cannula. In a preferred embodiment, the cannula openings have a width of from about 50 to 300 μm to ensure that adiabatic expansion occurs upon exit of a gas.

In a preferred embodiment, there is essentially no or negligible adiabatic expansion outside the application site, e. g. outside the nasopharynx or other appropriate sites, i. e. upon leaving the bottle and entering the cannula.

In a further preferred embodiment, the device has a tube extending into the pressurized bottle. The tube serves as in-flow of the gas during operation, e. g. when a fluid connection between a cannula and the pressurized bottle is established. Preferably, the tube extends not deeper into the bottle, than half its potential filling height, i. e. the height of the bottle measured vertically from, for example, shoulders of the bottle up to its bottom. This can serve at preventing the liquefied gas to exit the bottle when the fluid connection between a cannula and the pressurized bottle is opened instead of the gaseous phase.

In a further preferred embodiment, a first small quantity of liquefied gas can exit the bottle before the gas exits the bottle. This is useful for providing a fast initial cool down. This can be accomplished by providing a cup around the inlet of the tube in the inside of the bottle. Upon shaking or upon filling the bottle through said tube, a small quantity of liquid gas, preferably liquid $CO_2$ or $N2O$ remains in the cup. As soon as a fluid connection is established between the pressurized bottle and a cannula, i. e. the pressurized bottle is opened, this small quantity of liquefied gas exits the bottle and provides for a fast coolant effect in the patient's application area, e.g. the nasopharynx, the mouth or the lung.

Upon operation, the cannula in a first mode of application is inserted through the external nostrils into the patient's nasopharynx and gas is released to exit the pressurised gas container through the connection means into the cannula. The gas adiabatically expands in the patient's nasopharynx upon exiting through the cannula openings. This results in an immediate cooling effect on the tissue of the nasopharynx and in ultimate proximity to the patient's brain. Cooling of the carotid provides a further brain cooling effect.

According to an alternative mode of operation, a cannula may be inserted into the mouth of the patient up to the oropharynx. Upon release of the gas and by means of the adiabatic expansion, a cooling is achieved at the application site, i. e. within the oropharynx and the mouth cavity.

Though the mouth has a further distance with respect to the brain to be cooled, such an application at the mouth may have some advantages. A cooling within the mouth is easier, simpler and may be added to a nasal cooling and the cooling effect can be increased.

It is furthermore possible to release bigger amounts of gas in the mouth large cavity and the risk of icing at the application site is reduced. Furthermore, the application to the mouth may be easier than the application in the nose. Therefore, because of its simplicity, the application to the mouth can be easily performed by a non-trained medical personnel such as a family member or any lay person.

In a further mode, an application of the cannula in the trachea of the patient may be used to cool the lungs, e. g. in order to use the lungs as a heat exchanger to cool the whole body, to protect the myocardium as well as other organs such as kidney, liver and lung after resuscitation. Cooling the lungs and thus protecting the myocardium and other organs may be done in combination with the brain cooling through application of the inventive device in the mouth and/or in the nose but also can be used independently.

According to still a further preferred embodiment of the invention, the device may comprise fixation means for fixing the cannula on an application site of the patient's body.

Typically, the fixation means may also comprise sealing elements for sealingly attaching the cannula to an application site. Sealing members may e. g. be formed by a rubber band closing the mouth of the patient.

The device can be easily stored at ambient temperature and there is no further need of coolant means or gases potentially hazardous for the patient or the environment, such as for example per fluorocarbon.

In a further preferred embodiment, the cannula is essentially straight or has a radius of curvature of up to 20 mm.

In a further preferred embodiment, the device comprises a tube for intubation which is arranged to receive the at least one cannula.

According to a further preferred embodiment of the invention, the cannula comprises an internal, preferably essentially rigid inner tube and an external, preferably essentially soft, external tube, wherein said inner tube and external tube comprise at least one lumen. Preferably, the inner tube comprises a first lumen and the external tube comprises a second lumen, whereby preferably the first and second lumens are in fluid connection by means of openings on the inner tube. Even more preferably, the first and second lumens are further adapted to be brought into fluid connection with the nasopharynx by means of openings on the external tube.

Alternatively, the second lumen comprises an outlet for removal of the gas, e.g. the carbon dioxide.

Such arrangement allows adiabatic expansion of the pressurized gas from the first lumen to the second lumen, thereby providing a cooling effect while contact between the pressurized gas, e.g. $CO_2$, and the patient is prevented or reduced.

Preferably, the external tube comprising a second lumen is adapted to receive or comprise a solid or liquid, e.g. $H_2O$. More preferably, the solid or liquid in the second lumen has a comparably high specific thermal capacity, i.e. a solid or liquid absorbing more thermal energy without a substantial temperature increase than a majority of solids or liquids, preferably between 100 to 5000 J/(kg·K), more preferably between 2000 to 4500 J/(kg·K), most preferably between 2060 to 4185 J/(kg·K) in normal conditions of temperature and pressure. Even more preferably, the external tube encompassing the second lumen is substantially impermeable for liquids and gases during its intended use.

Such liquid in the second lumen has the advantage that the gas undergoing an adiabatic expansion upon exiting the inner tube through the openings is cooling down the liquid while the latter is functioning as a storage medium for the generated cold. Thus, the cooling effect may advantageously be extended even after emptying the gas bottle.

Upon adiabatic expansion of the pressurized gas from the first lumen to the second lumen and the associated generation of cold, ice formation of the liquid within the second lumen may occur.

On the other hand, the pressurized gas within the first lumen before any adiabatic expansion has been influenced by the outside temperature on the way between the pressurized gas container and the cannula thereby causing melting of such generated ice.

Furthermore, melting of the ice and increasing temperature of thereby generated liquid generally leads to a volume dilatation of such liquid. Volume dilatation of such liquid further induces breakage of ice neighbouring such liquid.

Such mechanism of icing of the liquid and melting respectively breakage in particular at the distal end of the cannula is important allowing a steady circulation of the gas. A varying gas ($CO_2$) flow may be observed by means of a flow meter.

A eutectic liquid may be provided in the second lumen, e.g. a solution of sodium chloride, in order to decrease the icing temperature.

Still more preferably, the sheath of the external tube is comprised by a flexible, in particular expandable, material. An expandable sheath of the external tube has the advantage that upon expansion of the external tube when gas is supplied to the second lumen, the cannula can be brought in direct contact with the tissue of the patient, in particular with the tissue of the nasopharynx and/or mouth of the patient.

Preferably, the device comprises a pressure valve arranged at an outlet of the second lumen and adapted to control the flow of the gas outside the second lumen. More preferably, the device is further adapted to control the gas flow between the first and second lumens.

Such arrangement allows the adjustment of a gas flow between the first and second lumen which is higher than the gas flow through the pressure valve leading to a controllable expansion of the external tube.

Preferably, the cannula is received at least along the total length of the tube. More preferably, the end of the tube at the far side of the distal end of the cannula is outside the head of the patient. Preferably, such tube is a tracheal tube.

Such arrangement has the advantage that cold may still be administered by the cannula while there is still access to the lungs of the patient for artificial ventilation, preferably artificial ventilation with $O_2$ or a mixture of $O_2$ and $N_2O$.

In a further aspect of the invention, a device is provided comprising a pressurized gas container and an inflatable bag, whereby the inflatable bag comprises a substantially closed sheath adapted to form an outer cooling contact surface upon inflation, and whereby the pressurized gas container and the inflatable bag are adapted to provide a cooling effect in the bag upon release of gas, e.g. by adiabatic expansion of the gas or mixture of gases.

WO 2006/000006 A2 proposes external cooling of a patient by means of an inflatable bag and a pressurized gas container storing liquid air, wherein, however, the inflatable bag fully envelopes the patient resulting in a direct contact between vaporized liquid air and the patient.

An arrangement with such an inflatable bag with an outer cooling surface advantageously results in an external cooling of the patient while the chest of the patient is still available e.g. for resuscitation.

Preferably, the inflatable bag is adapted to form a tub upon inflation to surround substantially the patient on the rear and lateral side.

More preferably, the inflatable bag is adapted to form a tub upon inflation to surround substantially the patient on the rear and lateral side leaving the head and arms outside. Such a form of the inflatable bag has the advantage that the arms are available for intravenous liquid administration. Even more preferably, the inflatable bag is formed as sleeveless vest to be wrapped around the patient.

Still more preferably, at least one tube may be arranged within the bag, in particular at the walls of the bag, and the at least one tube is inflatable upon release of gas from the pressurized gas container. Preferably, the tube comprises at least one opening which is adapted to enable an adiabatic expansion of the gas when exiting the tube through the opening thereby providing a cooling effect.

Cooling of the bag may be achieved upon release of the gas, e.g. $CO_2$, into the bag and/or such tube within the bag comprising at least one opening adapted to enable adiabatic expansion of the gas. The bag may be inflated by pressurized gas from the pressurized gas container and/or additionally inflated by a pressurized gas from an additional gas source.

Even more preferably, a pressurized gas container and an inflatable bag are functionally connected either directly or by means of a flexible tube.

Such inflatable bag has the advantage that external cooling of the patient's body can be achieved. It can be easily used in combination with a cooling cannula as shown above thereby using a pressurized fluid container for achieving multiple cooling effects. However, such a bag cooled by a pressurized gas is also advantageous without such a cannula.

In a further preferred embodiment, the gas container is adapted to hold a gas or mixture of gases chosen from the group consisting of oxygen, nitrogen, carbon dioxide, nitrous oxide, helium, neon, argon, krypton and xenon. Preferably, the mixture of gases is oxygen, carbon dioxide, nitrous oxide and argon. In a preferred embodiment, the carbon dioxide or nitrous oxide is pressurized in the bottle such as to liquefy. The bottle thus contains a liquid phase of carbon dioxide or nitrous oxide and a gaseous phase of oxygen, argon, nitrous oxide and carbon dioxide. The pressure in the bottle ensures the gases are propelled out of the bottle upon operation, i. e. establishing a fluid connection between the cannula and the pressurized bottle through opening the connection means. The gases are preferably medical grade.

The pressurized gas bottle is chosen in size, such as to hold preferably volume of from 0.5 to 5 liters, more preferably 1 l. It has been found, that 500 g of liquefied $CO_2$ is enough to provide 267 liters of $CO_2$ after expansion, for instance.

A cooling effect because of the change of the liquid to a gaseous state may also occur at the pressurized gas bottle attached to the cannula.

In a further aspect of the invention, a device is provided comprising a pressurized gas container and at least one cannula, wherein the pressurized gas container and/or parts of the cannula are substantially encompassed by a means for the retrieval of cold.

Preferably, the means for the retrieval of cold is provided by a serpentine coiled around the pressurized gas bottle and/or the cannula. Preferably, the serpentine is a flexible tube. The fluid within the serpentine may be a gas such as $O_2$ supplied at low pressure.

Alternatively, the means for the retrieval of cold may be provided by a hollow jacket. Preferably, the jacket has entry and exit ports, one of which is functionally connected to the cannula, in particular by a flexible tube and the other to a source of gas such as $O_2$.

More preferably, the pressurized gas bottle and/or the cannula is encompassed by a thermal insulation layer. Even more preferably, the serpentine is encompassed by a thermal insulation layer.

The arrangement of a serpentine supports the retrieval of cold.

Still more preferably, the serpentine is functionally connected to a cannula as shown hereinabove for providing additional cold to a patient, thereby used in combination. However, such means for retrieval of cold is also advantageous without the cannula as shown hereinabove providing cold to a separate cannula.

The fluid passing through the serpentine is cooled and may be used for additionally cooling the patient. This can e.g. be achieved by administering the cooled fluid (which may be $O_2$) to the patient. Alternatively, the cooled fluid may also be provided to cool a bag as described above.

Preferably, the additional cold administered by the serpentine may be provided by a connection means between the serpentine and the inside of the cannula. Such arrangement has the advantage that the pressurized gas can be cooled before the adiabatic expansion at the distal end of the cannula.

Alternatively, a separate cannula is arranged at the end of the serpentine for usage at an application site. Preferably, such cannula of the serpentine may be arranged in parallel to the cannula which is connected to the pressurized gas container.

Furthermore, the arrangement of thermal insulation layer encompassing the serpentine reduces the introduction of ambient heat to the surface of the serpentine or hollow jacket. Preferably, the thermal insulation layer is composed of expanded or extruded polystyrene.

Alternatively or additionally to the retrieval of the cold, the pressurized gas bottle may be formed in such a way that it can be positioned at an external application site of the patient. The external application site may be the neck of the patient. This results in an additional external cooling.

Preferably, the pressurized gas bottle generating cold may be encompassed by a casing sized and shaped for the usage as neck pillow. More preferably, the casing of the bottle is essentially of a flexible and heat conductive material, such as metal or composite to allow an efficient transfer of the cooling energy to the patient.

In a further preferred embodiment, the device comprises two cannulas instead of one. The cannulas are then adapted for insertion into one nasal opening each.

In a further preferred embodiment, the device is also equipped with a temperature sensor. The temperature sensor is preferably close or at the distal end of the cannula.

Further preferred embodiments encompass an electrical controller or regulator for regulating and adjusting the volume per minute of gas exiting the pressurized bottle, the desired temperature and/or the length and duration of gas exit. It has been found to be further advantageous to provide a feedback mechanism and auto regulatory function in feedback with a sensor at the distal end of the cannula. By such means, a desired temperature in the nasopharynx or oropharynx can be compared with the actual temperature achieved. Safety mechanisms can thus further be included for preventing the cooling to go below a certain threshold.

Said electrical controller or regulator can be equipped with a power supply. For that end, regular power supplies, such as lithium batteries have proven to be efficient.

In a further aspect of the invention, a device comprises a pressurized gas container with at least one cannula for application of a gas or mixture of gas to an application site and an atomizer, wherein the atomizer is arranged at the cannula.

Preferably, the atomizer is adapted to atomize a fluid containing an active pharmaceutical ingredient such as an antibiotic. More preferably, the atomizer is connected by a tube to a gas source, preferably a source of $CO_2$ and/or $O_2$, for atomizing the fluid. A further tube may be arranged at the atomizer for providing the fluid from a fluid source. Even more preferably, the atomizer is arranged at the distal end of the cannula.

Such arrangement of an atomizer allows the transport and application of an active pharmaceutical ingredient to a preferred body part of the patient, e.g. the lungs in case of pneumonia or to prevent pneumonia. This is advantageous since pneumonia is the most frequent complication reported after therapeutic cooling of a patient as provided by the present invention. Thus, it is the role of the atomizer to spread an antibiotic or similar bactericide for the prevention of an infection.

It can easily be used in combination with a cooling cannula as shown above thereby simultaneously providing an active pharmaceutical ingredient next to the cooling of the patient. However, an atomizer without a cannula providing cooling to a patient is also advantageous.

Another aspect of the present invention provides a set for intracorporally and preferably intranasally and/or intra mouthly cooling the brain of the patient. The set is particularly useful for installation into a first-aid facility such as an emergency car or a fixed or movable first-aid station. The set comprises a device as previously described with a pressurized gas container for containing a gas or a mixture of gases, at least one cannula for introduction into a patient's opening, e. g. the nasopharynx or oropharynx and adapted to provide for adiabatic expansion of the gas or mixture of gases upon exit from the cannula. The set further comprises a gas source for loading said device with a gas or mixture of gases. The gas source can be a source of a gas or mixture of gases chosen from the group of: oxygen, carbon dioxide, helium, neon, argon, nitrous oxide, krypton and xenon.

In a preferred embodiment, the gas source is a source of oxygen, carbon dioxide, nitrous oxide and argon.

In the context of the present invention, several mixtures of gases have proven to provide the desired effect. In a preferred embodiment, the gas or mixture of gases does not contain any per fluorocarbon.

In a further preferred embodiment, the mixture of gases comprises oxygen in an amount of from 1 to 99% of the total volume, preferably of 5% to 50%, more preferably of 30%.

In a still further preferred embodiment, the pressurized gas container is adapted to receive a mixture of liquid $CO_2$ or liquid $N_2O$ and liquid $O_2$ or liquid $N_2$.

Preferably, the pressurized gas container is adapted to receive a mixture of liquid $CO_2$ or liquid $N_2O$ and liquid $O_2$ or $N_2$ in a non-closed state of the pressurized gas container.

Mixing liquid $O_2$ or $N_2$ to the liquid $CO_2$ or liquid $N_2O$ in the pressurized gas container results in an increase of the vapour pressure established in the ullage of the pressurized gas container.

Preferably, a stabilizing agent is added to the mixture of liquid $CO_2$ or liquid $N_2O$ and liquid $O_2$ or $N_2$ into the pressurized gas container. The stabilizing agent may be an inert material, preferably in powder form.

The mixture of liquids in the pressurized gas container in a non-closed state may leak out during handling. A stabilizing agent in the mixture of liquids may work as a sponge, thereby reducing the risk of leakage and facilitating the handling of the pressurized gas container.

A non-closed state of the pressurized gas container means within the present invention that in normal use, the content of the pressurized gas container is essentially not sealed to the environment by a closing means.

Since the bottle is occupied by an inert material working as a sponge, the liquefied gas is prevented to exit the bottle instead of the gaseous phase when the fluid connection between a cannula and the pressurized bottle is opened.

The storage of a gas or mixture of gas in liquid form such as liquid $O_2$ or liquid $N_2$ may be guaranteed by maintaining a sufficient cooling and/or a sufficient pressure in a storage means.

Since storage of the mixture in a non-closed state of the pressurized gas container only allows storage of a gas at low pressure, low temperature has to be established in the pressurized gas container. Preferably, the pressurized gas container comprises a thermal isolation layer adapted to allow the storage of a mixture of liquid $CO_2$ or liquid $N_2O$ and liquid $O_2$ or liquid $N_2$ in a non-closed state of the pressurized gas container at a temperature of −196° C. Such thermal isolation layer of the pressurized gas container may be comprised by expanded polystyrene.

A sufficiently low temperature, gas pressurized at up to 1000 bar may be achieved in the ullage of the pressurized gas container by limiting the passage of the gas flow outside the pressurized gas container by the closing means.

Preferably, the pressurized gas container is adapted for sufficient isolation against upper outside temperatures of about 70 to 80° C. This has the advantage that the pressurized gas container can be used in ambulances. Typically, containers of other sources of gas such as $N_2O$ are used in ambulances which may advantageously stabilize the storage temperature of the pressurized gas container.

In a preferred embodiment, at least one of the gas or mixture of gases in the gas source is stored as a liquid. For that end, the gas needs to be under sufficient pressure to be stored as a liquid in the pressurized bottle. Means for converting gases into the liquid state are known. For the sake of the present invention, pressurization is the preferred way of storing the gases in the pressurized gas container.

In a preferred embodiment, $CO_2$ or N2O is pressurized at around 60 bar, such as to be present in liquid state in the gas source.

One further aspect of the present invention is a method for providing intracorporal cooling of a patient, in particular for providing intranasal or intra mouth cooling to the brain of a patient. This method is particularly useful for a patient suffering from cardiovascular emergency. A device for cooling the brain as previously described is provided. At least one cannula of said device is inserted through the external nostrils into the patient's nasopharynx. A gas or a mixture of gases is provided to exit the at least one cannula by opening a connection means between cannula and pressurized gas container. The gas is cooled by means of adiabatic expansion upon exiting the cannula and entering the nasopharynx of the patient in one mode of operation.

According to an alternative mode of operation, the cannula is inserted into the mouth of the patient. Upon release of the gas through the cannula and by means of adiabatic expansion the gas is cooled and thereby cools the patient's brain.

In still a further alternative mode of operation a cannula is inserted into the trachea of a patient and produces a cooling effect on the patient's lung upon exiting the cannula.

While these alternative application sites (mouth and trachea) are also preferred in context with cooling by means of adiabatic expansion it will be appreciated that also other fluids for achieving cooling might be used, e. g. liquids generating cold upon evaporation such as liquid $CO_2$, liquid nitrous oxide, ether, acetone or perfluorocarbons.

According to still a further aspect of the invention there is provided a device which comprises a source of fluid adapted to generate cool upon application from the source. According to this aspect of the invention the device is adapted to be applied to a patient's mouth or to the patient's trachea.

Accordingly, still a further aspect of the invention is directed to a method for providing intracorporal cooling to a patient wherein a fluid is applied to an application site of the patient. The fluid is adapted to generate cold upon application. The application site is selected from the mouth or the trachea of the patient.

In a preferred embodiment, the method is performed with a mixture of gases selected from the group consisting of:

oxygen, nitrogen, carbon dioxide, helium, neon, argon, nitrous oxide, krypton and xenon. Preferably, the method is performed with oxygen and at least one further gas of said group.

In a further preferred embodiment, at least one noble gas is used in addition to oxygen.

In a preferred embodiment, the liquid phase consists of liquid $CO_2$, or liquid $N_2O$ and the gaseous phase of gaseous $O_2$, $CO_2$ nitrous oxide, and Ar. Upon opening a fluid connection between the pressurized bottle and the cannula, the mixture in the gaseous phase exits first, whereas liquid $CO_2$ or nitrous oxide of the liquid phase evaporates and resupplies the $CO_2$ or nitrous oxide content of the gaseous phase. In this manner, $CO_2$ or nitrous oxide serves as propellant for the gas as well as coolant, by means of adiabatic expansion upon exiting the device. It further means that initially a comparatively higher relative amount of $O_2$ and Ar is supplied to the patient, which has been found favourable for its oxygenizing and neuroprotective effect.

A further aspect of the invention is directed to a method. The method comprises coupling of a pressurized gas container with an inflatable bag. Pressurized gas from the pressurized gas container is supplied to the inflatable bag by opening a connection means for providing a cooling effect to a patient.

Preferably, the pressurized gas is cooled by a cooling means to provide external cooling to a patient. More preferably, the cooling effect is achieved by adiabatic expansion of the gas.

A further aspect of the invention is directed to a method for applying an active pharmaceutical to an application site. The method comprises the steps of coupling a pressurized gas container and at least one cannula (8) for application of a gas or mixture of gas to an application site. In a further step, an atomizer is connected to the cannula and operated for applying the active pharmaceutical ingredient to the application site.

A further aspect of the invention is directed to a method for providing intracorporal cooling to a patient. A pressurized gas container and at least one cannula are coupled. The pressurized gas container and/or parts of the cannula are encompassed by a means for the retrieval of cold.

The invention will be further outlined in the following reference to preferred embodiments with examples and drawings, without being limited thereto.

FIG. 1: shows a schematic drawing of a pressurized bottle according to the present invention FIG. 2: shows a schematic drawing of a cross-section of the head of a patient with an inserted cannula according to the present invention FIG. 3: shows a schematic drawing of the distal end of a cannula according to the present invention FIG. 4: shows a schematic representation of a set with a gas source and a device according to the present invention.

FIG. 5: shows a schematic drawing of a pneumatic switching circuit for a device according to the present invention FIGS. 6a and 6b: show fixation means for fixing a cannula to a patient's nose FIGS. 7a and 7b: show fixation means for fixing a cannula to a patient's mouth FIGS. 8a and 8b: show a first embodiment of an extension at the distal end of a cannula FIGS. 9a and 9b: show a second embodiment of an extension applied the distal end of the cannula FIGS. 10a and 10b: show a schematic cross sectional and top view of a distal end of the cannula FIG. 11: shows a schematic cross sectional view of a proximal end of the cannula FIG. 12: shows a schematic view of a device for tracheal application.

FIG. 13: shows a schematic view of a pressurized bottle with a serpentine and a thermal insulation layer FIG. 14: shows a schematic view of a pressurized bottle with a jacket and a thermal insulation layer FIG. 15: shows a schematic representation of an inflatable bag connected with a pressurized gas container FIG. 16: shows a cross-sectional view through the inflatable bag connected with the pressurized gas container FIG. 17: shows a schematic drawing of a cross-section of the head of a patient with an inserted tracheal tube surrounding the cannula for intramouth cooling and ventilation FIG. 18: shows a schematic drawing of an inserted tracheal tube with the cannula applied within the lumen of a tracheal tube FIG. 19: shows a schematic drawing of the distal end of a cannula according to the present invention with liquid in a second lumen FIG. 1 shows a pressurized gas bottle 1 made of metal or composite material, containing a pressurized gas in a liquid phase 2, carbon dioxide, nitrous oxide and gaseous phase 3, carbon dioxide, oxygen, nitrogen, nitrous oxide and argon. A metallic or PVC connection tube 4 extends into the interior hollow space of the pressurized bottle 1. The pressurized bottle 1 is required to be able to resist pressures of at least 100 bar.

A gate valve 5 is operably placed between a duct 30 and the pressurized bottle 1 and is used to trigger the discharge of the gas into the cannula 8 (not shown in FIG. 1) through the duct 30 and a flexible wire-mesh reinforced tube 31. The flexible tube 31 has a length of 30 cm. A check valve 6 serves for one-way filling the bottle with the gas or mixture of gases or liquefied gases (see also FIG. 5). In case of excess pressure inside the bottle, such as resulting from improper storage or excess ambient heat, safety valve 7 decompresses the gases and prevents explosion. The pressurized bottle 1 is adapted to hold an equivalent volume of 1 liter of the pressurized mixture of gases and has dimensions of 25 cm height and 10 cm width. Gate valve 5, duct 30, check valve 6 and safety valve 7 form a connection means 32 between the flexible tube 31 and the pressurized bottle 1 that reduces to a negligible degree adiabatic expansion of the gas upon opening the gate valve 5 and conducts the gas into the cannula 8 (not shown in FIG. 1). The distal end 9 of the duct 30 is barbed, such as to enable stably fitting the flexible tube 31 onto the duct 30.

In the present example, the mixture of gases consists of oxygen, nitrogen, carbon dioxide, nitrous oxide, and argon. A liquid phase 2 consists mainly of liquid carbon dioxide or nitrous oxide. A gaseous phase 3 consists of gaseous carbon dioxide or gaseous nitrous oxide, gaseous oxygen, gaseous nitrogen and gaseous argon. The gases are medical grade gases. Medical grade gases and pressure bottles 1 can be supplied by Linde Group, Munich (DE) for instance.

A tube 4 extends from the connection means 32 into the inside of the pressurized bottle 1. In the present embodiment, the tube 4 has a slightly pointed tip and is covered by a cap 10, which semi-circularly encases the tip, such as to leave a pocket between the tip and the cap 19. The cap 10 thus forms a cup around the tip of the tube 4. Upon shaking the pressurized bottle, this cap 10 fills with a small quantity liquid $CO_2$ or nitrous oxide 33, thus providing for a first shot of liquid $CO_2$ or nitrous oxide to the patient upon opening of the gate valve 5. This shot provides for a first rapid cooling effect, after which the gaseous phase 3 is released from the bottle. As the gaseous phase 3 initially holds a high content of $O_2$ and argon at higher pressure than $CO_2$ and/or nitrous oxide, this provides the further positive effect to the patient of oxygen and Argon neuroprotective effect supply early on. The cup typically may have a volume of about 0.5 ml. In a preferred embodiment, the cap may be adapted to hold a quantity of liquefied gas between 0.5 and 2 ml, in particular of liquid $CO_2$ or $N_2O$.

The tube 4 is constructed, such as to prevent to dip into the liquid phase 2. The filling level b of the pressurized bottle is half or less than half the bottle height a, thereby accidentally releasing liquid $CO_2$ or nitrous oxide is prevented regardless of the bottle position.

The cannula 8 with a proximal end 8" and a distal end 8' is shown inserted in a human patient's 12 nasopharynx 13 in FIG. 2. The cannula 8 is inserted with distal end 8' first through the external nostrils 11 of the patient 12 into the nasopharynx 13. The pressurized gas exits the cannula at its distal end 8' and by means of adiabatic expansion cools the surrounding region. This creates a cool atmosphere in the nasopharynx 13 and provides a coolant effect through heat transfer cools the cranium postero-inferior bone 14, thereby causing a coolant effect on the brain 15.

The cannula 8 in the present example is of a semi-rigid material, either metal or plastic (PVC) for example, and coated with silicone rubber as an external tube. The silicone rubber can be a replaceable single use coating facilitating lubrification and insertion through the nostrils.

Upon opening the valve, a temperature of around 0.5° C. of the $CO_2$ is achieved upon exit at the distal end 8' of the cannula 8.

The cannula is shown in further detail in FIG. 3. The distal end 8' of the cannula consists of a silicone rubber external tube 18 around a semi-rigid plastic (PVC) internal tube 17. A lumen 16 has a fluid connection with the outside by means of openings 21 in the semi-rigid plastic tube 17 and holes 20 in the external silicone rubber tube 18. Furthermore, the construction can provide for a further interior lumen between the semi-rigid plastic tube 17 and the external silicone rubber tube 18, thereby causing the gas to undergo a main adiabatic expansion in said further interior lumen upon exiting the semi-rigid plastic tube 17 and a second minor adiabatic expansion upon exiting the external silicone rubber tube 18. This enables the cooling effect to be more evenly distributed.

A set according to the invention is shown in FIG. 4. The device 22 for cooling intra nasally the brain, consisting essentially of a cannula 24, a connecting means 25 and a pressurized gas container 26 can be functionally connected to a gas storage means 23 containing a mixture of gases, preferably a mixture of carbon dioxide or nitrous oxide and oxygen. This results in a set 27 for intranasally cooling the brain or the mouth.

FIGS. 6a and 6b schematically show a cannula 8 applied to the patient 12 through the nostrils 11. The cannula 8 is fixed at this site by means of a strap 40. The strap 40 e. g. may comprise a Velcro arrangement for quick application and release. The cannula 8 may be attached to the strap 40 by means of glue 41.

FIGS. 7a and 7b show a fixation device for applying a cannula 8 to the mouth of a patient. The cannula 8 is held in place at the mouth of a patient by means of a strap 50 which can be fixed around the head of the patient by means of e. g. a Velcro fixation. The strap 50 is provided with a sealing mask 52 made of rubber which can be sealingly applied to the patient's mouth. The cannula may be attached to the sealing member 52 by means of glue 51.

In order to avoid closing of a distal orifice 19 of the cannula 8 as it is shown in FIGS. 8a and 8b, an extension is provided. The extension is made in the form of a cap 34 comprising one arch 35 arranged at the distal end 8' of the cannula 8 on opposite sites of the distal opening 19. The arch 35 avoids closing of the distal orifice 19 by contact of the distal end 8' of the cannula 8 with parts of the patient's body.

FIG. 8b shows a top view to the distal end of the cannula. The arch 35 bridges the distal opening 19 of the cannula without closing it.

FIGS. 9a and 9b show an alternative embodiment with three arches which are arranged circumferentially at 120° whereas the embodiment of FIG. 8b shows an arrangement at 180° with one single arch 25.

The arches according to FIG. 8a and FIG. 9a may be provided in a cap 34 which can be made separately from the cannula and which may be attached to the distal end of the cannula 8. Typically, such cap may be made of a plastic material by injection moulding or also may be formed as a metal piece.

Figure 10A:
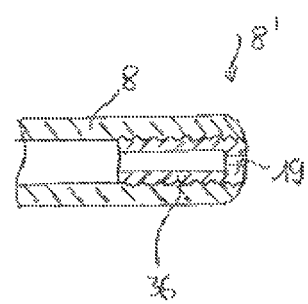
Figure 10B:
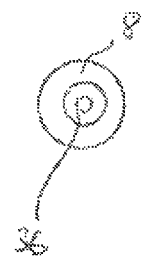

FIGS. 10a and 10b show an alternative embodiment of a distal end of a cannula. The cannula 8 is made of a plastic material and at the distal end of the cannula 8 there is arranged a metal insert 36. The metal insert 36 has a reduced cross section at its distal end thereby forming the distal orifice 19. The metal insert 36 has a contoured outer circumferential surface allowing a friction and/or form-fit connection with the inner surface of the cannula 8. It is furthermore possible to also apply arches as shown in FIG. 8a or FIG. 9a in combination with the insert shown in FIG. 10a. The arches may be integrally formed with the insert 36 or as a separate piece.

Figure 11:
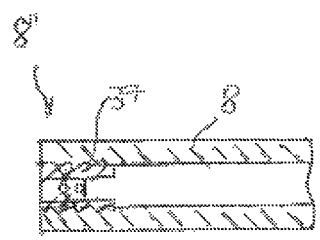

FIG. 11 schematically shows the cross section of a cannula 8 at its proximal end. The proximal end 8" of the cannula 8 is provided with an insert 37 having a reduced diameter d. The diameter d is chosen such as to avoid adiabatic expansion when the fluid passes through the insert 37. However, the diameter d is chosen such as to limit the pressure within the lumen of the cannula 8.

Figure 12:
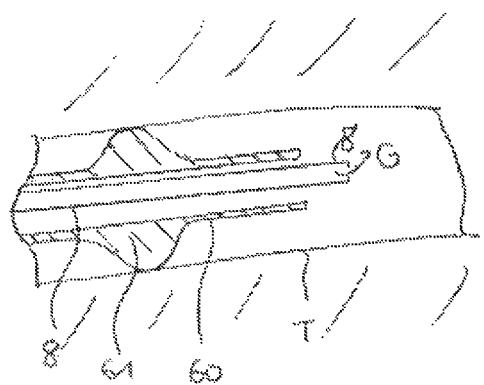

FIG. 12 shows an alternative application of the cannula 8 according to the invention. The cannula 8 is applied within the lumen of an endotracheal tube 60 within the trachea T. The endotracheal tube is a standard tube which can be applied to the trachea e. g. through a laterally cut incision which may be provided by first aid personnel. The endotracheal tube is provided with a cuff 61. The cannula 8 may be inserted through the tube to the application site shortly before the bifurcation of the trachea for cooling the lungs of a patient. If gas G exits the cannula 8 because of adiabatic expansion, the area close to the distal end 8' of the cannula is cooled. It is of course also possible to use specifically suitable tubes for application of the cannula 8 in the trachea. Also instead of a gas cooling upon adiabatic expansion liquids carrying a cooling effect upon evaporation may be used.

While FIG. 12 only shows application at the trachea, it is of course understood that such a cooling may be used in combination with cooling in the nasopharynx or in the mouth as it has been shown hereinabove.

Figure 13:
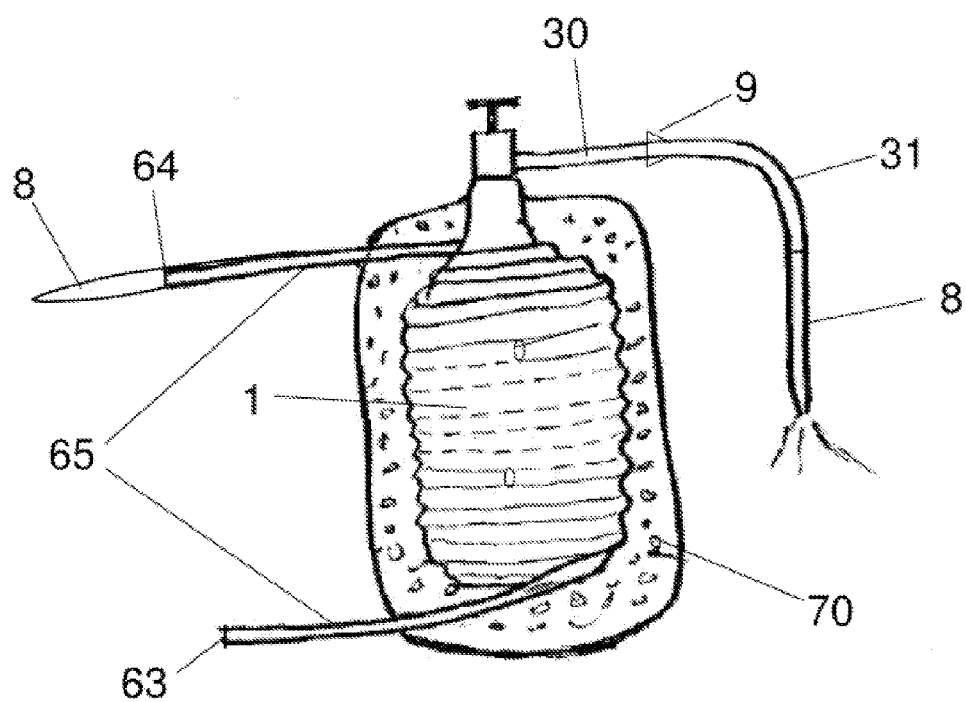

FIG. 13 shows the pressurized bottle 1 with a serpentine 65. The serpentine 65 is formed by a flexible tube which is coiled around the pressurized gas bottle 1. Such flexible tube has a diameter of 6 mm and is composed of a plastic material. The fluid passing through the serpentine 65 is $O_2$ supplied from a source of $O_2$, e.g. a pressurized $O_2$ bottle. An inlet side 63 of the serpentine 65 connects the serpentine 65 to a source of $O_2$ (not shown in FIG. 13) whereas an outlet side 64 of the serpentine 65 is connected to a separate cannula 8. Thereby, additional cooled gas is administered to the gas or mixture of gas exiting the cannula on one end. FIG. 13 further shows a thermal insulation layer 70 encompassing the serpentine 65 and the neck of the pressurized bottle 1. The thermal insulation layer 70 is composed of expanded or extruded polystyrene.

Figure 14:
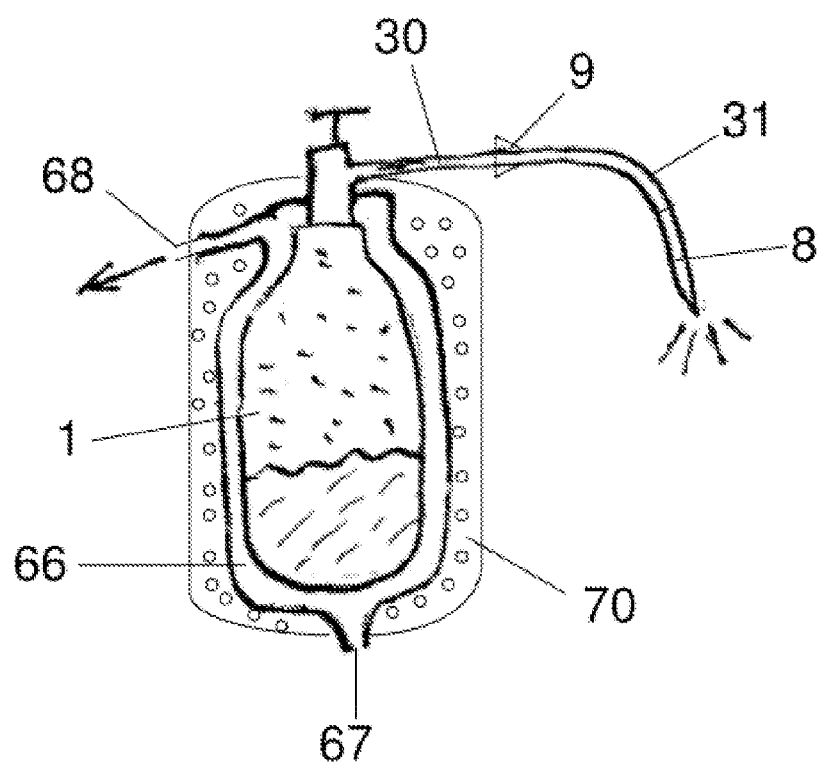

FIG. 14 shows a hollow jacket 66 around the pressurized bottle 1. The jacket 66 and the neck of the pressurized bottle 1 is encompassed by the thermal insulation layer 70. The hollow jacket 66 has an entry port 67 and an exit port 68 for supplying a cooling fluid in a similar manner as shown in context with FIG. 13. The entry port 67 is connected to a source of $O_2$ (not shown in FIG. 14). The exit port 68 is connected to the cannula (not shown in FIG. 14) to provide additional cooling to a patient.

Figure 15:
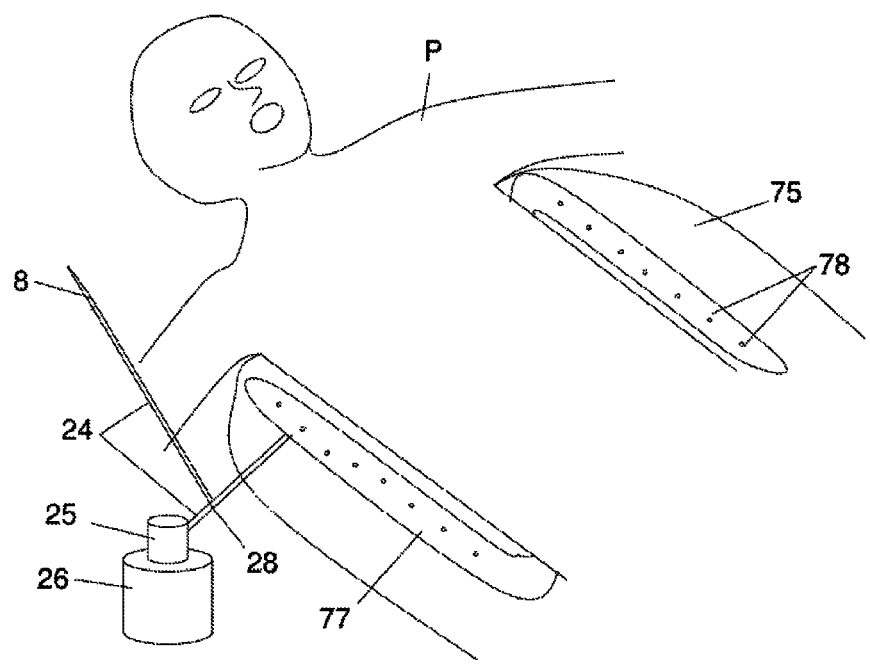

FIG. 15 shows a pressurized gas container 26 which is connected by a connecting means 25 and a flexible tube 24 with the cannula 8. The flexible tube 24 further comprises a branch 28 for connecting the pressurized gas container 26 with a tube 77 of an inflatable bag 75 as well. The tube 77 is coiled along the patient-sided wall of the inflatable bag 75. Pressurized gas entering the tube 77 inflates the latter. Upon inflation the pressurized gas expands adiabatically through the openings 78 of the tube 77 thereby cooling the patient P externally. The inflatable bag 75 and the tube 77 can be made of rubber while the rubber may be reinforced by tissue. The inflatable bag 75 forms a tub surrounding the patient on the rear and lateral side. The head and both arms are left outside of the bag 75 and the arms remain available for intravenous liquid administration.

Figure 16:
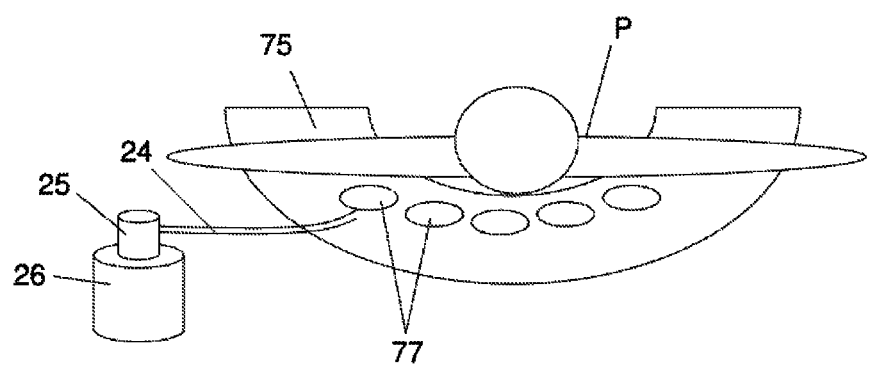

FIG. 16 shows a cross-sectional view through the inflatable bag 75 whereby the tube 77 of the inflatable bag 75 is connected with the pressurized gas container 26 by a flexible tube 24 and a connecting member 25. The head and both arms of the patient P are left outside of the bag 75. The tube 77 of the inflatable bag 75 is arranged along the patient-sided wall of the inflatable bag 75 for efficient external cooling of the patient P.

Figure 17:
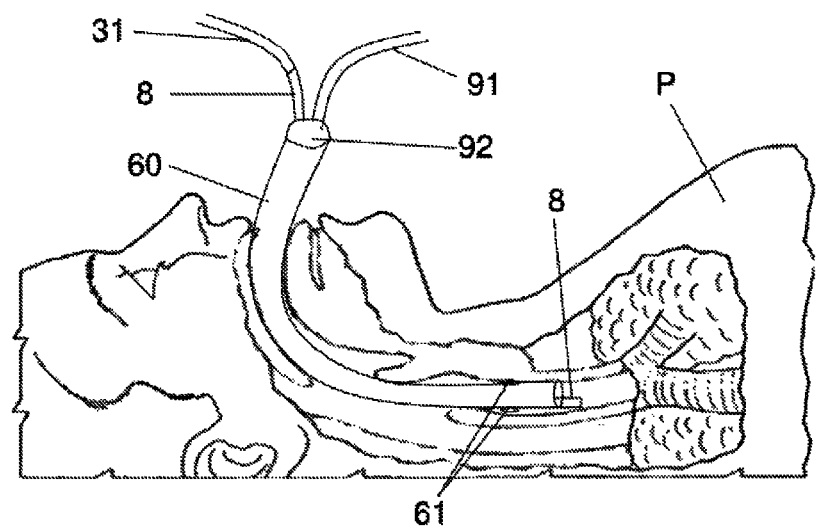

FIG. 17 shows a schematic drawing of a cross-section of the head of a patient. A tracheal tube 60 is inserted through the mouth of the patient surrounding the cannula 8 as shown in FIG. 12. The far side of the tube at the far side of the distal end of the cannula is outside the head of the patient. The tracheal tube is provided with a cuff 61. The cannula 8 is inserted through the tube to the application site shortly before the bifurcation of the trachea for cooling the lungs of the patient. The tracheal tube 60 comprises a branch 92 with an inlet for sealingly arranging the cannula 8 and an inlet for sealingly arranging a ventilation tube 91. The arrangement of the ventilation tube 91 at the tracheal tube 60 allows access to the lungs of the patient for artificial ventilation while cold is administered by the cannula 8. The tracheal tube 60 is essentially of a flexible material such as polyvinylchloride (PVC) and/or polypropylene (PP).

Figure 18:
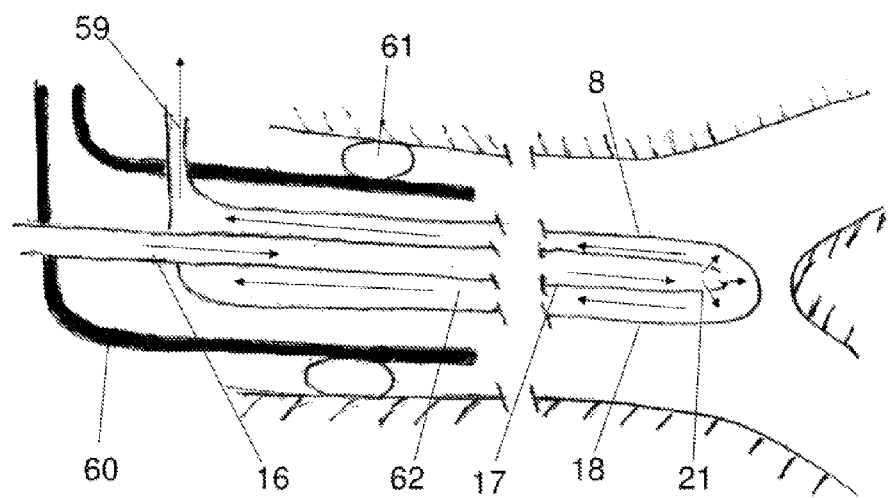

FIG. 18 shows a schematic drawing of a tracheal tube 60 inserted into the trachea of a patient as shown in FIG. 12 or 17 with the cannula 8 applied within the lumen of a tracheal tube 60. The distal end 8' of the cannula 8 consists of an external tube 18 around the internal tube 17 which has already been shown in FIG. 3. The lumen 16 has a fluid connection with a further interior lumen 62 between the internal tube 17 and external tube 18 by means of openings 21. The external tube 18 is of a soft material such as silicone. The gas undergoes an adiabatic expansion upon exiting the internal tube 17 through the openings 21 into the further interior lumen 62. The further interior lumen 62 comprises an outlet 59 for removal of the gas, e.g. the $CO_2$, thereby preventing or minimizing contact between the gas and the patient.

Figure 1:
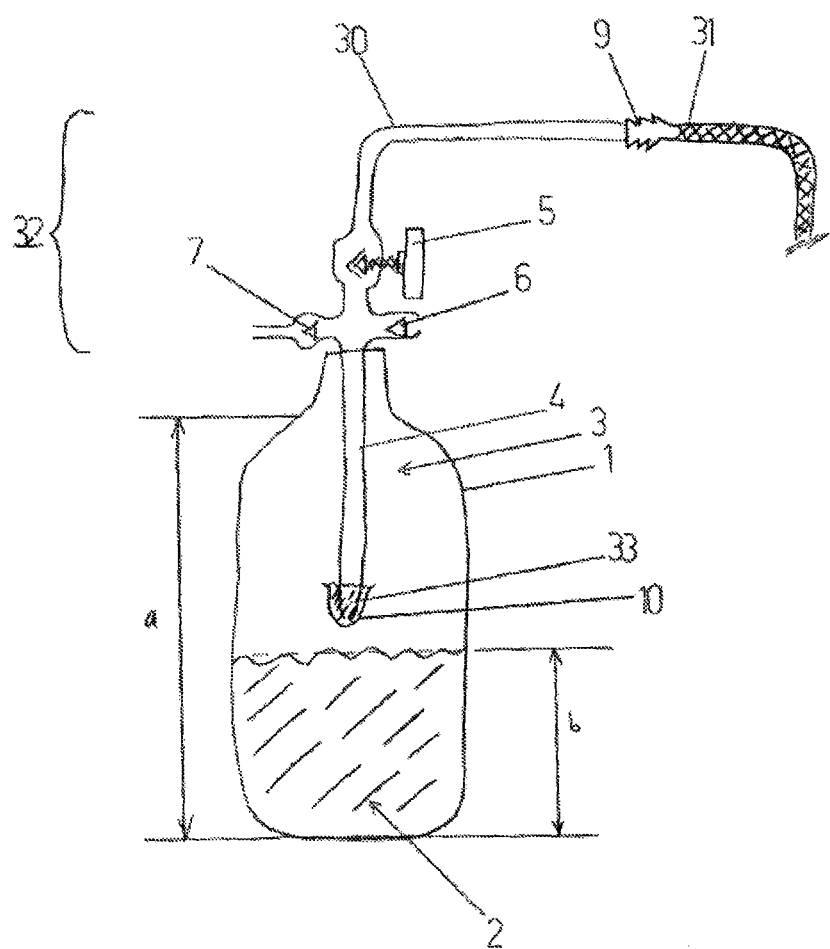
Figure 2:
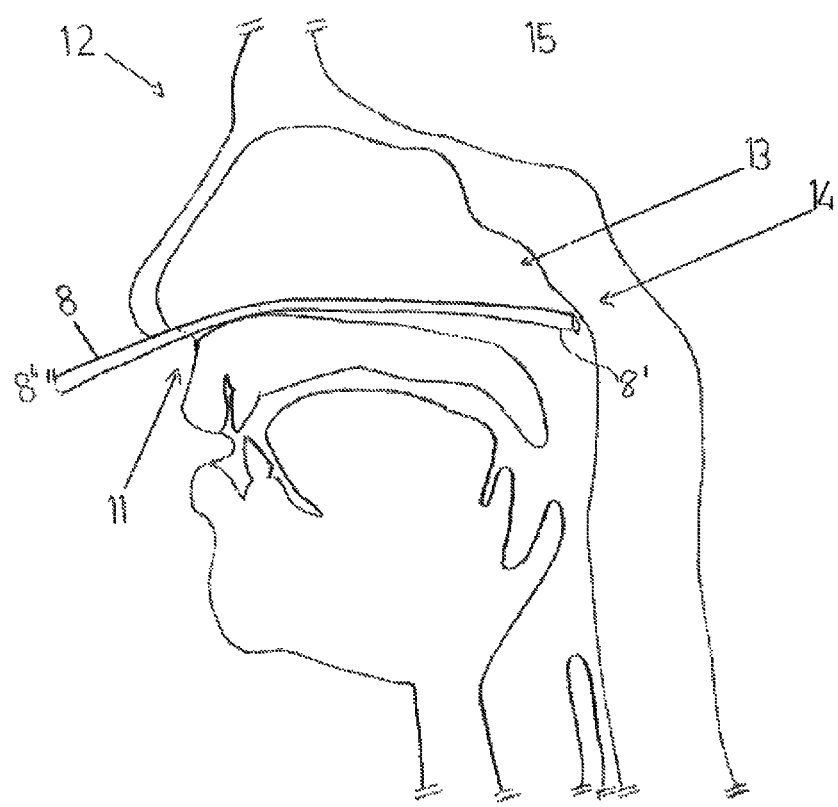
Figure 3:
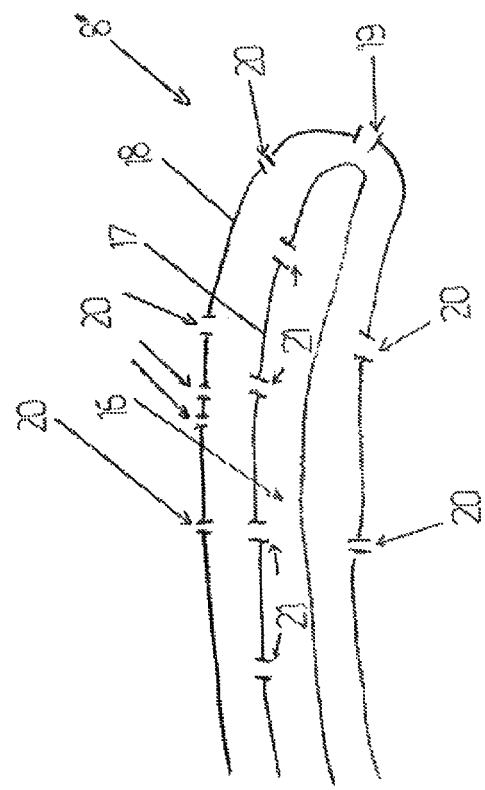
Figure 4:
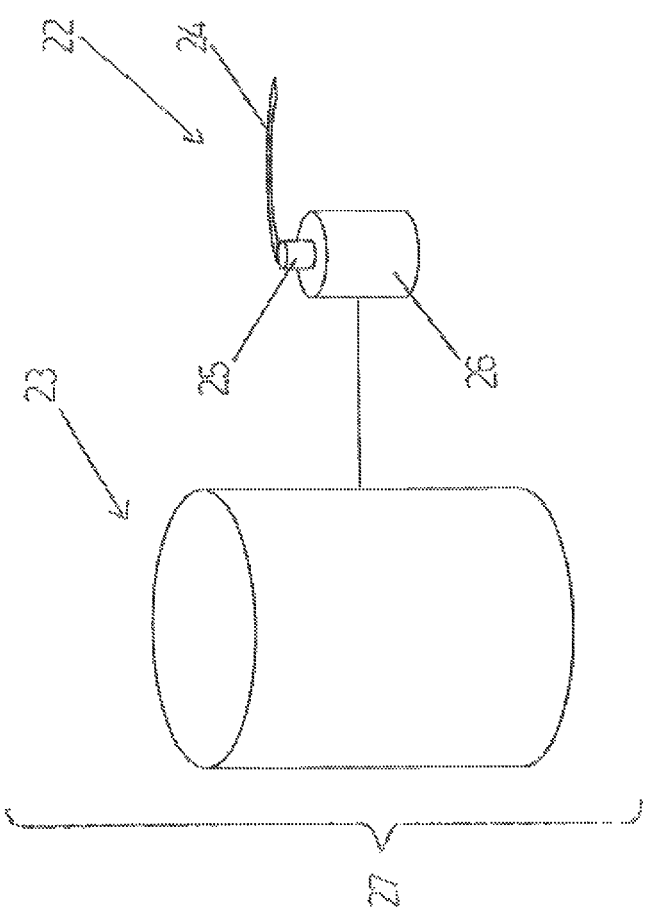
Figure 5:
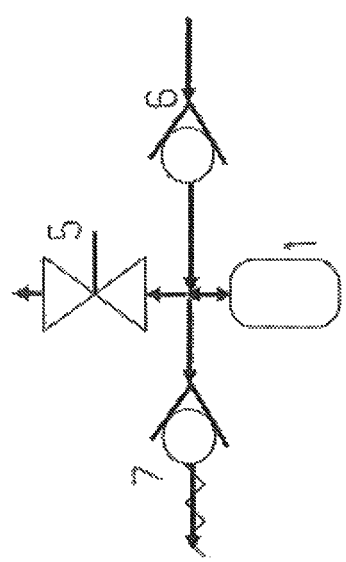
Figure 19:
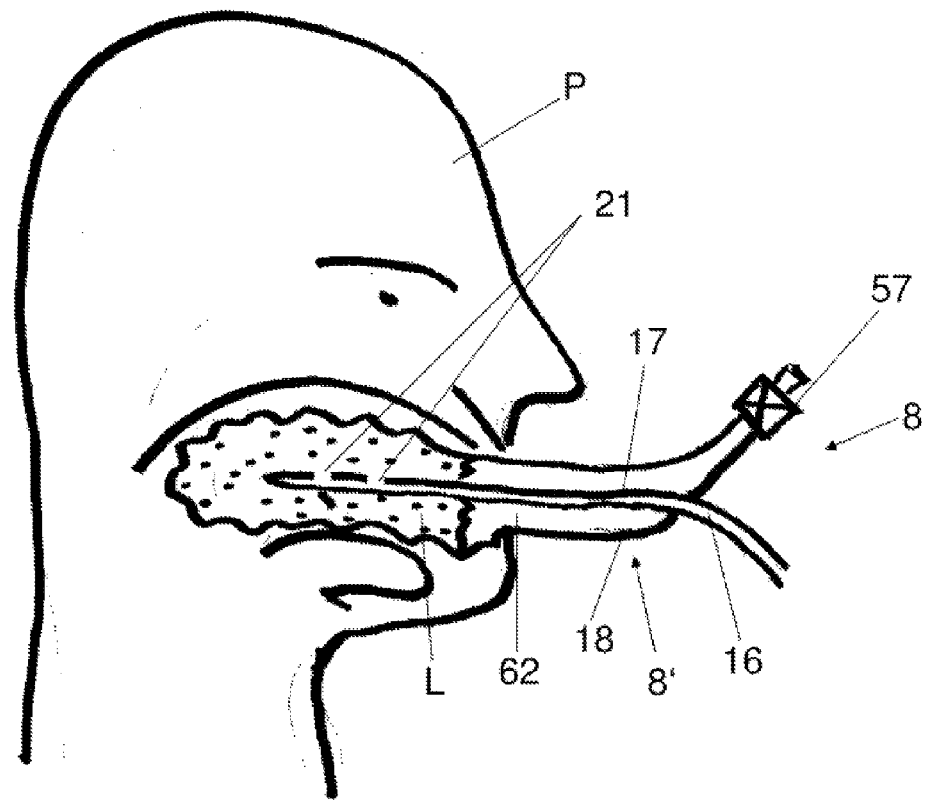

FIG. 19 shows a schematic drawing of the distal end 8' of the cannula 8 as already shown in FIG. 3 and FIG. 18 comprising an external tube 18 around the internal tube 17. The first lumen 16 has a fluid connection with the second lumen 62 between the internal tube 17 and the external tube 18 by the means of openings 21. The second lumen 62 is adapted to receive a liquid L such as water. The liquid may be already present in the second lumen 62 before the operation of the device. The gas undergoing an adiabatic expansion upon exiting the internal tube 17 through the openings 21 is cooling down and freezing the water, wherein the latter is functioning as a storage medium for the cold. The openings 21 may be adapted to be permeable substantially only for the gas and not for the liquid. A pressure valve 57 is arranged at an outlet for the gas which controls the flow of the gas outside the second lumen. An adjustment of a gas flow between the first and second lumens which is higher than the gas flow through the pressure valve 57 leads to a controllable expansion of the external tube 18. FIG. 19 shows an expanded external tube 18 which is brought in direct contact with the tissue of the mouth of the patient P.

The invention claimed is:

1. A device for providing cooling intracorporally comprising:
   a pressurized gas container for containing a gas or a mixture of gases, and at least one cannula with a lumen and a proximal opening and at least one distal opening for application to an application site,
   wherein the pressurized gas container and the at least one cannula are:
   (i) first connected by connection means, and said connection means being adapted to substantially prevent adiabatic expansion of the gas, or mixture of gases, upon passage of the gas, or the mixture of gases, from the container to the at least one distal opening of the at least one cannula, and
   (ii) second facilitate adiabatic expansion of the gas, or the mixture of gases, upon exiting of the gas, or mixture of gases, from the at least one cannula, and
   the at least one opening has a width of from about 50 to 300 μm so as to minimize adiabatic expansion of the gas, or the mixture of gases, prior to exiting from the at least one cannula and ensure that the adiabatic expansion of the gas, or the mixture of gases, substantially occurs upon exiting of the gas, or the mixture of gases, from said at least one distal opening of the at least one cannula.

2. The device according to claim 1, suitable for providing cooling nasally to the brain of a patient, wherein the at least one cannula is suitable for introduction into the patient's nasopharynx, the patient's mouth or the patient's trachea.

3. The device according to claim 1, wherein said at least one cannula is semi-rigid.

4. The device according to claim 1, wherein the at least one cannula is between 50 mm and 200 mm long.

5. The device according to claim 1, wherein the cannula has a distal end provided with an extension projecting from said distal end.

6. The device according to claim 5, wherein said extension is formed as at least one arch projecting from said distal end.

7. The device according to claim 5, wherein said extension is formed by a cap attached to the end of said cannula, and said cap comprising at least one opening on an outer surface thereof.

8. The device according to claim 1, wherein said cannula is made of a plastic material and a metal insert is arranged at the distal end of the cannula, and said metal insert forming said distal opening.

9. The device according to claim 1, wherein said cannula comprises a wall having a thickness chosen such that said cannula withholds a pressure of at least twice the maximum pressure within said gas container.

10. The device according to claim 1, wherein said cannula comprises, adjacent to its proximal end, a pressure limiting member having a reduced diameter (d) such that no adiabatic expansion occurs upon passage of said gas or mixture of gases from the container through the connection means to said pressure limiting member.

11. The device according to claim 1, wherein the at least one cannula comprises at least one further opening.

12. The device according to claim 1, wherein the at least one cannula is essentially straight or has a radius of curvature of about up to 20 mm.

13. The device according to claim 1, wherein the gas container comprises a pressurized gas, or mixture of gases, chosen from the group consisting of oxygen, nitrogen, carbon dioxide, helium, neon, argon, nitrous oxide, krypton and xenon.

14. The device according to claim 13, wherein the gas container comprises a pressurized gas, or mixture of gases, chosen from the group consisting of oxygen, nitrogen, carbon dioxide and argon.

15. The device according to claim 5, wherein said device comprises two cannulas for insertion into both nasal openings of the patient.

16. The device according to claim 1, wherein said device comprises fixation means for fixing said cannula on an application site on a patient's body.

17. The device according to claim 16, wherein said fixation means further comprise sealing means for sealingly attaching said cannula to the application site.

18. The device according to claim 1, wherein the cannula comprises an internal inner tube and an external tube and said inner tube and external tube comprise at least one lumen.

19. The device according to claim 18, wherein the inner tube is essentially rigid and the external tube is essentially soft.

20. The device according to claim 18, wherein the external tube is adapted to receive or comprise a solid or liquid.

21. The device according to claim 20, wherein the solid or liquid received or comprised by the external tube has a specific thermal capacity between 100 to 5000 J/(kg·K).

22. The device according to claim 18, wherein a sheath of the external tube comprises a flexible material.

23. The device according to claim 22, wherein said device comprises pressure valve arranged at an outlet of a second lumen and adapted to control the flow of the gas outside the second lumen.

24. The device according to claim 1, wherein said device has a tube extending into the pressurized bottle, and the tube does not extend beyond half of a filling height (b) of a maximum filling height (a) of the bottle.

25. The device according to claim 24, wherein the tube has a cap surrounding its tip and said cap is adapted to hold a quantity of liquefied gas.

26. The device according to claim 1, wherein said device comprises a tube for intubation arranged to receive at least one cannula.

27. The device according to claim 1, comprising a pressurized gas container and an inflatable bag, wherein the inflatable bag comprises a substantially closed sheath adapted to form an outer cooling contact surface upon inflation, and the pressurized gas container and the inflatable bag provide a cooling effect in the bag upon release of gas from the container.

28. The device according to claim 27, wherein the pressurized gas container and the inflatable bag provide a cooling effect in the bag upon release of gas from the container by means of adiabatic expansion of the gas or mixture of gas.

29. The device according to claim 1 comprising a pressurized gas container and at least one cannula for application of a gas, or mixture of gas, to an application site, wherein the device comprises an atomizer arranged at the cannula.

30. The device according to claim 1 comprising a pressurized gas container and at least one cannula, wherein at least one of the pressurized gas container and parts of the cannula are substantially encompassed by a means for retrieval of cold.

31. A set for cooling intra nasally the brain of a patient comprising: a device according to claim 1, and a gas source for loading said device with a gas, or mixture of gases, or liquefied gases wherein said gas source is a source of a gas, or mixture of gases, chosen from the group of oxygen, nitrogen, carbon dioxide, helium, neon, argon, nitrous oxide, krypton and xenon.

32. The set according to claim 31, wherein the gas source is a source of a mixture of oxygen, carbon dioxide and argon.

33. The set according to claim 31, wherein the gas source is a source of a mixture of oxygen and at least one other gas selected from the group consisting of nitrogen, carbon dioxide, helium, neon, argon, nitrous oxide, krypton and xenon and an oxygen content in the mixture amounts to 1 to 99% of the total volume.

34. The set according to claim 31, wherein the gas, or mixture of gases, in the gas source is stored as a liquid.

35. Method for providing intracorporal cooling of a patient comprising the steps of: a) Providing a device for cooling according to claim 1; b) Inserting at least one cannula of said device into said patient's body; c) Providing a gas or a mixture of gases to exit the at least one cannula by opening a connection means between the cannula and a pressurized gas container, and whereby the gas is cooled by means of adiabatic expansion upon exiting the cannula and entering the nasopharynx of the patient.

36. The method of claim 35, suitable for providing intranasal cooling of the brain of a patient, wherein said at least one cannula of said device is inserted into said patient's body through the external naris into the patient's nasopharynx.

37. The method of claim 35, wherein the mixture of gases is a mixture of gases selected from the group consisting of oxygen, nitrogen, carbon dioxide, nitrous oxide, helium, neon, argon, krypton and xenon.

38. The method of claim 35, wherein at least one cannula is coupled to a tube for intubation receiving the at least one cannula.

39. A method for providing intracorporal cooling to a patient, comprising the steps of a) providing a set for cooling according to claim 31; b) applying a fluid to an application site, said fluid being adapted to generate cold upon application to the application site, wherein said application site is selected from the patient's mouth or the patient's trachea.

40. A method for providing external cooling to a patient comprising the steps of: (a) providing a set for cooling according to claim 31; (b)(a) coupling the pressurized gas container and an inflatable bag; (c) supplying pressurized gas from the pressurized gas container to the inflatable bag for providing a cooling effect to the patient.

41. The method of claim 40, wherein the cooling effect is achieved by adiabatic expansion of the gas.

42. A method for applying an active pharmaceutical ingredient to an application site comprising the steps of: (a) providing a set for cooling according to claim 31; (b) coupling the pressurized gas container and at least one cannula for application of a gas or mixture of gas to an application site; (c) connecting an atomizer at the cannula, and (d) operating the atomizer.

43. A method for providing intracorporal cooling to a patient comprising the steps of: (a) providing a set for cooling according to claim 31; (b) coupling the pressurized gas container and at least one cannula, and (c) encompassing at least one of the pressurized gas container and parts of the cannula by a means for the retrieval of cold.

\* \* \* \* \*